(12) United States Patent
Dewey

(10) Patent No.: US 8,034,020 B2
(45) Date of Patent: Oct. 11, 2011

(54) OPTICAL FLOW SENSOR

(75) Inventor: Paul Dewey, Poway, CA (US)

(73) Assignee: Carefusion 303, Inc., San Diego, CA (US)

( * ) Notice: Subject to any disclaimer, the term of this patent is extended or adjusted under 35 U.S.C. 154(b) by 165 days.

(21) Appl. No.: 12/142,215

(22) Filed: Jun. 19, 2008

(65) Prior Publication Data

US 2009/0318858 A1 Dec. 24, 2009

(51) Int. Cl.
*A61M 31/00* (2006.01)
(52) U.S. Cl. .......................................... 604/67
(58) Field of Classification Search ............... 604/67
See application file for complete search history.

(56) References Cited

U.S. PATENT DOCUMENTS

| 5,533,412 | A | 7/1996 | Jerman et al. |
| 6,304,328 | B1 * | 10/2001 | Longtin ..................... 356/445 |
| 6,386,050 | B1 * | 5/2002 | Yin et al. .................. 73/861.95 |
| 6,582,393 | B2 | 6/2003 | Sage, Jr. |

* cited by examiner

*Primary Examiner* — Nicholas D Lucchesi
*Assistant Examiner* — Jason Flick
(74) *Attorney, Agent, or Firm* — McDermott Will & Emery LLP

(57) ABSTRACT

An optical flow sensor is provided, including a heater configured to heat an aliquot of fluid in an adjacent fluid-delivery channel and a sensor disposed adjacent to the fluid-delivery channel downstream from the heater. The sensor is configured to illuminate fluid in the fluid-delivery channel, to collect reflected light from the illuminated fluid, and to determine when the heated aliquot passes the sensor based upon an amount of the reflected light. A method for determining a flow rate of a fluid is also provided. The method includes heating an aliquot of the fluid at a first position of a fluid-delivery channel, illuminating fluid in the fluid-delivery channel at a second position downstream from the first position, measuring an amount of light reflected from the illuminated fluid to determine a change in the amount corresponding to the heated aliquot passing the second position, and calculating the flow rate of the fluid based upon a distance between the first position and the second position and a time between the heating the aliquot and the heated aliquot passing the second position.

7 Claims, 6 Drawing Sheets

OPTICAL FLOW SENSOR

CROSS-REFERENCE TO RELATED APPLICATION

Not applicable.

STATEMENT REGARDING FEDERALLY SPONSORED RESEARCH OR DEVELOPMENT

Not applicable.

FIELD

Embodiments of the present invention generally relate to flow sensors and, in particular, relate to optical flow sensors.

BACKGROUND

Intravenous ("IV") fluid delivery systems are used to deliver fluids (e.g., medicines, transfusions, etc.) to patients at controlled rates. To accurately control IV fluid delivery, an open-loop control system may be used. An open-loop control system includes a processor that varies the speed of a relatively accurate fluid pump used to infuse a medicinal fluid into a patient based upon a predefined algorithm and as a function of various parameters, such as temperature, fluid type, and desired flow rate. These open-loop, processor-controlled pumping systems are generally expensive and complex. Moreover, compensation for variations in pump accuracy must be employed in such systems to achieve an acceptable level of accuracy. The rate of fluid delivery is also affected by the precision of disposable components used in the fluid path that conveys the fluid to the patient. Open-loop control systems are not capable of compensating for variations in the internal diameter and material hardness of fluid lines and pumping components, which may change over time as the components are repeatedly stressed. As a result, higher cost disposable components with tight tolerances must be used in such systems to avoid a loss of accuracy.

SUMMARY

Embodiments described herein address the foregoing problems by providing a low-cost, low-complexity system for delivery of medicinal fluids utilizing a closed-loop control system that provides high accuracy in the rate of fluid delivery to a patient. The closed loop system measures fluid flow rate using a low cost flow sensor and adjusts an inexpensive fluid delivery pump based upon the measured flow rate to achieve a desired flow rate. An inexpensive pump can be used in such a system, as the accuracy of the pump is not important to achieving a desired delivery rate. Similarly, the tolerance specifications of the disposable components used in the system can be greatly relaxed, as the closed-loop system can easily compensate for a lack of precision in these components. As most of the variables that are considered in algorithms employed for open-loop control can be ignored in a closed-loop controlled infusion system, the process control logic used in a closed-loop infusion system is relatively simple and easy to implement.

Certain embodiments provide an optical flow sensor. The sensor comprises a heater configured to heat an aliquot of fluid in an adjacent fluid-delivery channel, and a sensor disposed adjacent to the fluid-delivery channel downstream from the heater. The sensor is configured to illuminate fluid in the fluid-delivery channel, to collect reflected light from the illuminated fluid, and to determine when the heated aliquot passes the sensor based upon an amount of the reflected light.

Certain embodiments provide a method for determining a flow rate of a fluid. The method comprises heating an aliquot of the fluid at a first position of a fluid-delivery channel, illuminating fluid in the fluid-delivery channel at a second position downstream from the first position, measuring an amount of light reflected from the illuminated fluid to determine a change in the amount corresponding to the heated aliquot passing the second position, and calculating the flow rate of the fluid based upon a distance between the first position and the second position and a time between the heating the aliquot and the heated aliquot passing the second position.

Certain embodiments provide a medicinal fluid administering system. The system comprises a fluid delivery system for administering a fluid to a patient, and an optical flow sensor for measuring a rate of the fluid administered to the patient. The optical flow sensor comprises a laser configured to heat an aliquot of the fluid in an adjacent fluid-delivery channel, and a sensor disposed adjacent to the fluid-delivery channel downstream from the laser. The sensor is configured to illuminate the fluid in the fluid-delivery channel, to collect reflected light from the illuminated fluid, and to determine when the heated aliquot passes the sensor based upon an amount of the reflected light.

It is to be understood that both the foregoing summary and the following detailed description are exemplary and explanatory and are intended to provide further explanation of the embodiments as claimed.

BRIEF DESCRIPTION OF THE DRAWINGS

The accompanying drawings, which are included to provide further understanding of the invention and are incorporated in and constitute a part of this specification, illustrate embodiments of the invention and together with the description serve to explain the principles of the invention. In the drawings.

DETAILED DESCRIPTION

In the following detailed description, numerous specific details are set forth to provide a full understanding of the disclosed and claimed embodiments. It will be apparent, however, to one ordinarily skilled in the art that the embodiments may be practiced without some of these specific details. In other instances, well-known structures and techniques have not been shown in detail to avoid unnecessarily obscuring the disclosure.

Various approaches to fluid delivery employ different methods for measuring fluid flow rates. For example, one method, referred to as a thermal "time of flight" method, involves measuring the motion of a small heated volume of fluid down a flow path to determine a flow rate of the fluid. An aliquot of fluid is heated at a first position in the flow path, and at a predetermined second position downstream from the first, the passage of the heated aliquot of fluid is detected by a sensor. The sensor may measure different parameters of the fluid in the flow path to determine when the heated portion passes the sensor. For example, the sensor may shine a light through a fluid-delivery channel through which the fluid flows to determine when the heated aliquot passes. Because the temperature of a fluid changes the index of refraction thereof, the amount of light entering a photodetector will change as a heated fluid passes. For fluids whose index of refraction is a function of temperature, a measured change in index of refraction at the sensor indicates the passage of the heated aliquot of fluid. Such an approach may not work, however, with less-than-transparent fluids (e.g., translucent and opaque fluids such as lipids, packed cells, total parenteral nutrition ("TPN"), blood, breast milk, etc.).

Figure 1:
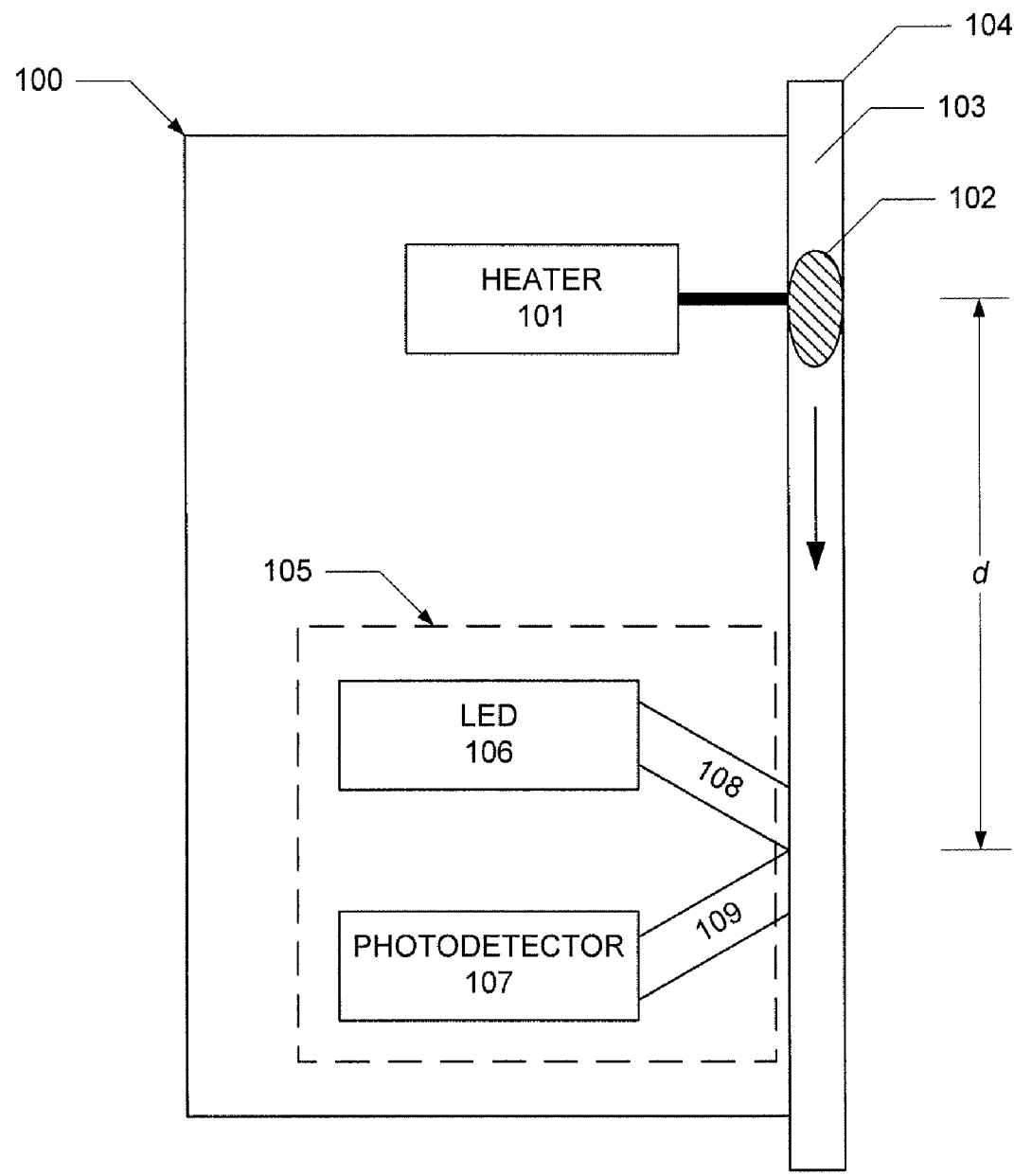
FIG. 1 is a block diagram illustrating an exemplary optical flow sensor according to certain embodiments.

According to certain embodiments, an optical flow sensor provides accurate measurement of flow rate for any fluid, whether opaque or transparent, at a relatively low cost. A block diagram illustrating an exemplary optical flow sensor according to certain embodiments is illustrated in FIG. 1. Optical flow sensor 100 includes a heater 101 configured to heat an aliquot 102 of fluid 103 in a fluid-delivery channel 104 adjacent to heater 101. According to one exemplary embodiment, heater 101 may be a laser. In accordance with certain other embodiments, heater 101 may be any one of a number of other heating devices, including electrical heaters, resistors, etc. Optical flow sensor 100 further includes a sensor 105 disposed adjacent to fluid-delivery channel 104 downstream a predetermined distance d from heater 101. Sensor 105 is configured to illuminate fluid 103 in fluid-delivery channel 104. According to certain embodiments, sensor 105 may illuminate fluid 103 with an LED 106. In accordance with certain other embodiments, sensor 105 may illuminate fluid 103 with any one of a number of other light sources, including, for example, a laser, an incandescent filament, a fluorescent bulb, etc. Moreover, sensor 105 may illuminate fluid 103 with radiation of any wavelength, including visible light, infrared, ultraviolet, etc.

Sensor 105 is further configured to collect reflected light from the illuminated fluid 103, and to determine when heated aliquot 102 passes sensor 105 based upon an amount of the reflected light. In this regard, sensor 105 may include a photodetector 107 optically coupled to fluid-delivery channel 104 with a polished fiber, a lens, a prism, or the like. In the present exemplary embodiment illustrated in FIG. 1, sensor 105 includes a first highly polished fiber 108 that optically couples LED 106 to fluid-delivery channel 104, and a second highly polished fiber 109 that optically couples photodetector 107 to fluid-delivery channel 104. According to certain embodiments, photodetector 107 may be an optical photodetector. In accordance with certain other embodiments, photodetector 107 may be any one of a number of other light or radiation sensors, including a photoresistor, a photovoltaic cell, a photodiode, etc.

As can be seen with reference to FIG. 1, both LED 106 and photodetector 107 are disposed on the same side of fluid-delivery channel 104. This arrangement allows optical flow sensor 100 to determine the flow rate of fluids not previously suitable for time-of-flight rate sensing, such as opaque fluids, non-homogenous fluids, non-Newtonian fluids and the like.

Figure 2:
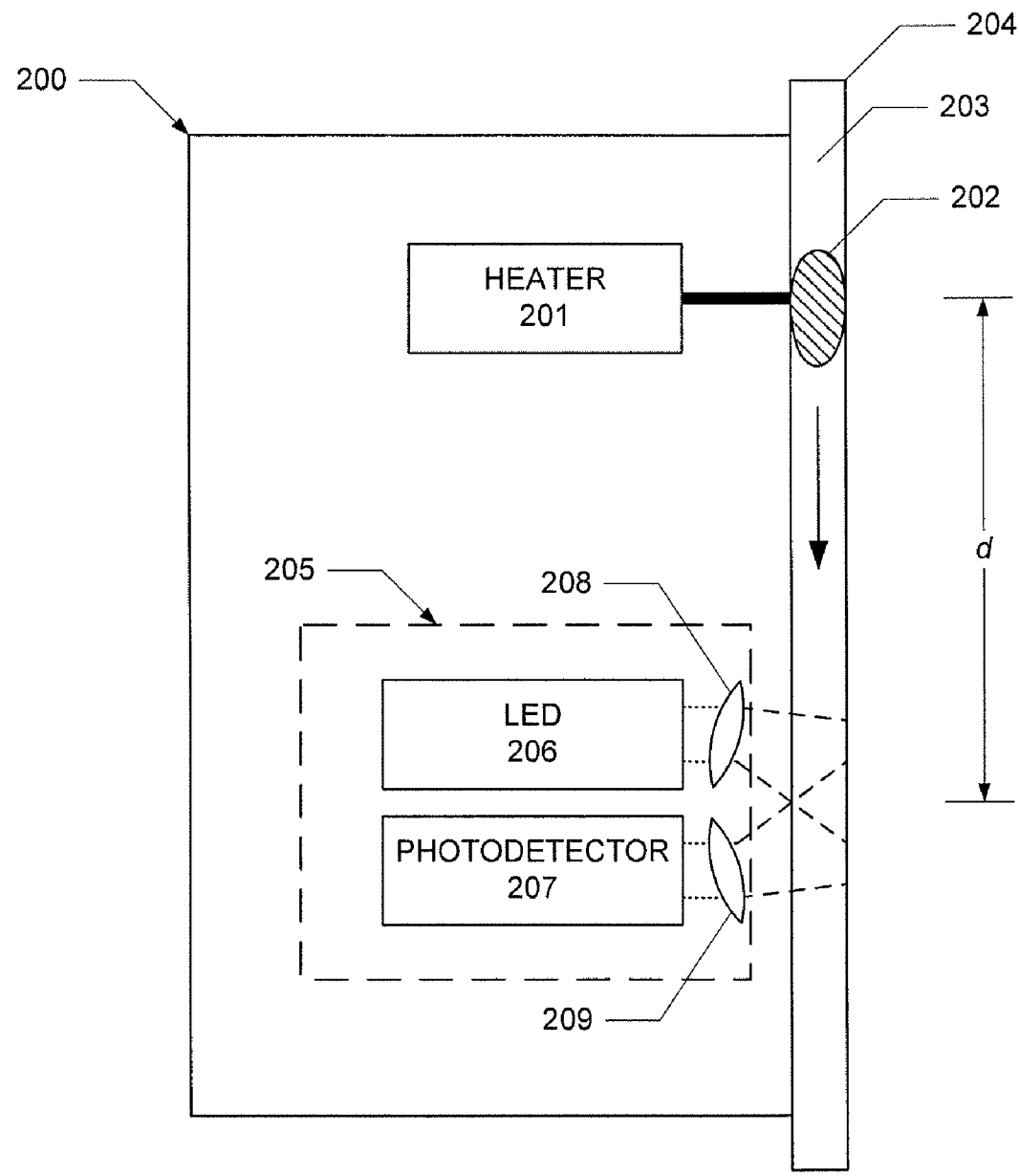
FIG. 2 is a block diagram illustrating an exemplary optical flow sensor according to certain embodiments.

FIG. 2 is a block diagram illustrating an optical flow sensor 200 according to another exemplary embodiment. Optical flow sensor 200 includes a heater 201 configured to heat an aliquot 202 of fluid 203 in a fluid-delivery channel 204 adjacent to heater 201. Optical flow sensor 200 further includes a sensor 205 disposed adjacent to fluid-delivery channel 204 downstream a predetermined distance d from heater 201. Sensor 205 is configured to illuminate fluid 203 in fluid-delivery channel 204 with an LED 206 optically coupled to fluid-delivery channel 204 with a lens 208. Sensor 205 is further configured to collect reflected light from the illuminated fluid 203, and to determine when heated aliquot 202 passes sensor 205 based upon an amount of the reflected light. In this regard, sensor 205 includes a photodetector 207 optically coupled to fluid-delivery channel 204 with a lens 209.

As can be seen with reference to FIG. 2, both LED 206 and photodetector 207 are disposed on the same side of fluid-delivery channel 204. This arrangement allows optical flow sensor 200 to determine the flow rate of fluids not previously suitable for time-of-flight rate sensing, such as opaque fluids, non-homogenous fluids, non-Newtonian fluids and the like.

Figure 3:
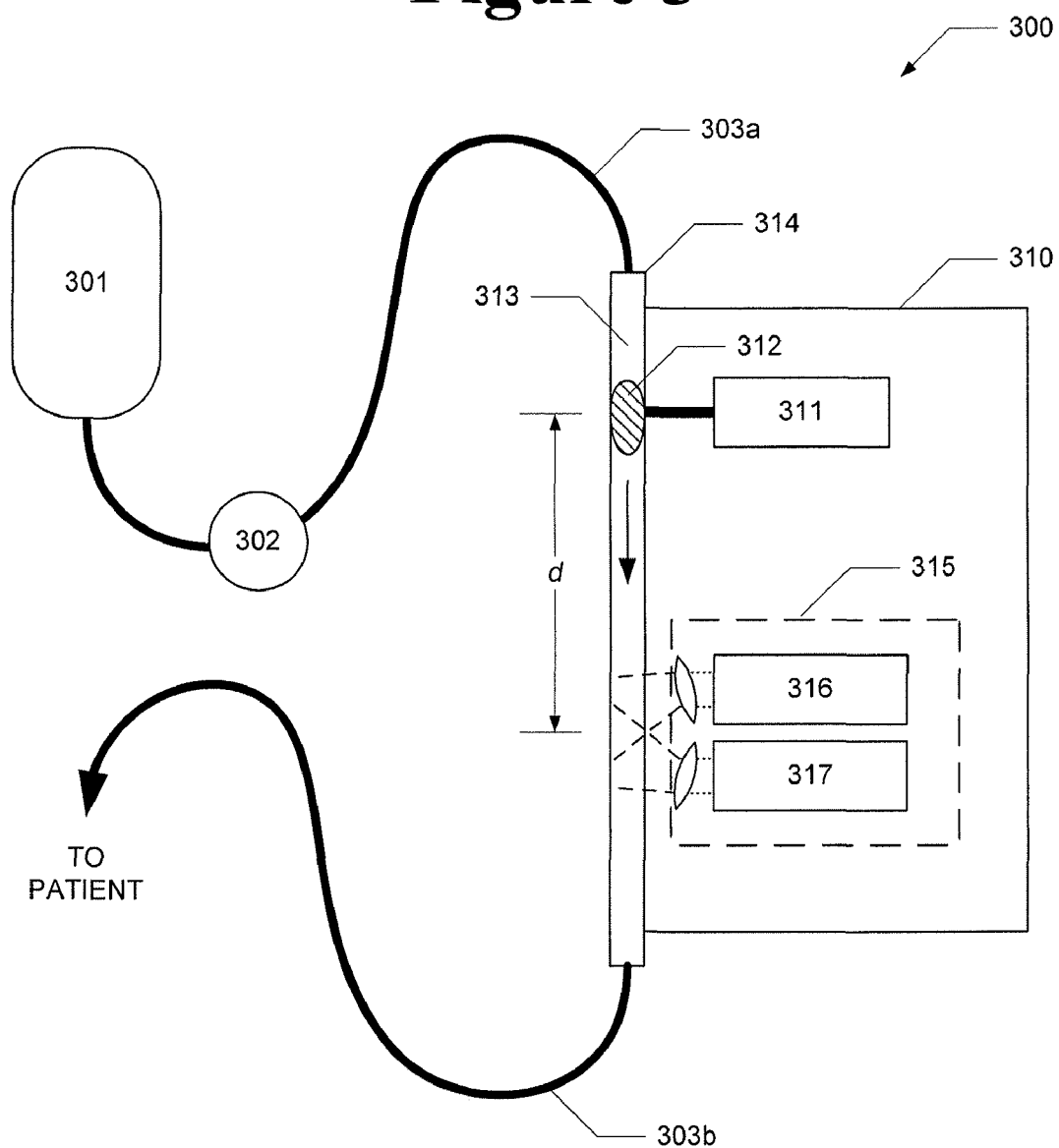
FIG. 3 is a block diagram illustrating a medicinal fluid administering system according to certain embodiments.

FIG. 3 illustrates a medicinal fluid administering system in accordance with one exemplary embodiment. Medicinal fluid administering system 300 includes a fluid delivery system for administering a fluid to a patient and optical flow sensor 200, which is configured to measure a rate at which the fluid is administered to the patient. The fluid delivery system includes a fluid reservoir 301, from which fluid 313 is pumped by a pump 302 through a fluid delivery path 303a to the optical flow sensor 310 and on (via delivery path 303b) to the patient. The optical flow sensor 310 includes a heater 311 configured to heat an aliquot 312 of fluid 313 in a fluid-delivery channel 314 adjacent to heater 311. Optical flow sensor 310 further includes a sensor 315 disposed adjacent to fluid-delivery channel 314 downstream a predetermined distance d from heater 311. Sensor 315 is configured to illuminate fluid 313 in fluid-delivery channel 314 with an LED 316 optically coupled to fluid-delivery channel 314 with a lens. Sensor 315 is further configured to collect reflected light from the illuminated fluid 313, and to determine when heated aliquot 312 passes sensor 315 based upon an amount of the reflected light. In this regard, sensor 315 includes a photodetector 317 optically coupled to fluid-delivery channel 314 with a lens.

Figure 4:
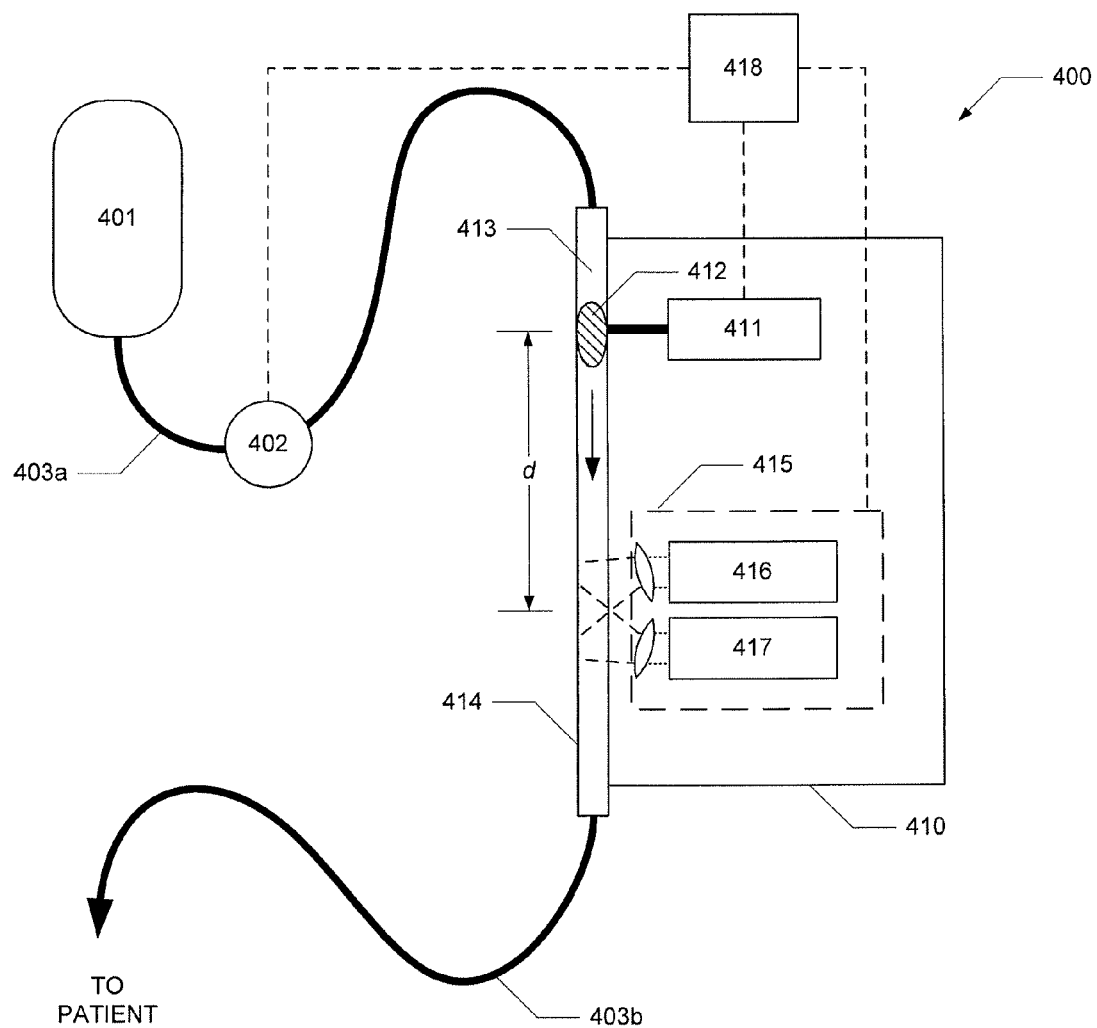
FIG. 4 is a block diagram illustrating a medicinal fluid administering system according to certain embodiments.

FIG. 4 illustrates a medicinal fluid administering system utilizing a closed-loop control system in accordance with one exemplary embodiment. Medicinal fluid administering system 400 includes a fluid delivery system for administering a fluid to a patient and optical flow sensor 200, which is configured to measure a rate at which the fluid is administered to the patient. The fluid delivery system includes a fluid reservoir 401, from which fluid 413 is pumped by a pump 402 through a fluid delivery path 403a to the optical flow sensor 410 and on (via delivery path 403b) to the patient. The optical flow sensor 410 includes a heater 411 configured to heat an aliquot 412 of fluid 413 in a fluid-delivery channel 414 adjacent to heater 411. Optical flow sensor 410 further includes a sensor 415 disposed adjacent to fluid-delivery channel 414 downstream a predetermined distance d from heater 411. Sensor 415 is configured to illuminate fluid 413 in fluid-delivery channel 414 with an LED 416 optically coupled to fluid-delivery channel 414 with a lens. Sensor 415 is further configured to collect reflected light from the illuminated fluid 413, and to determine when heated aliquot 412 passes sensor 415 based upon an amount of the reflected light. In this regard, sensor 415 includes a photodetector 417 optically coupled to fluid-delivery channel 414 with a lens. System 400 further includes a controller 418 configured to calculate a flow rate of fluid 413 based by dividing the time between heater 411 heating aliquot 412 and heated aliquot 412 being detected by sensor 415. Controller 418 may be further configured to adjust a pumping rate of pump 402 based upon a difference between the calculated flow rate and a desired flow rate (e.g., by reducing or increasing the pump speed).

Figure 5:
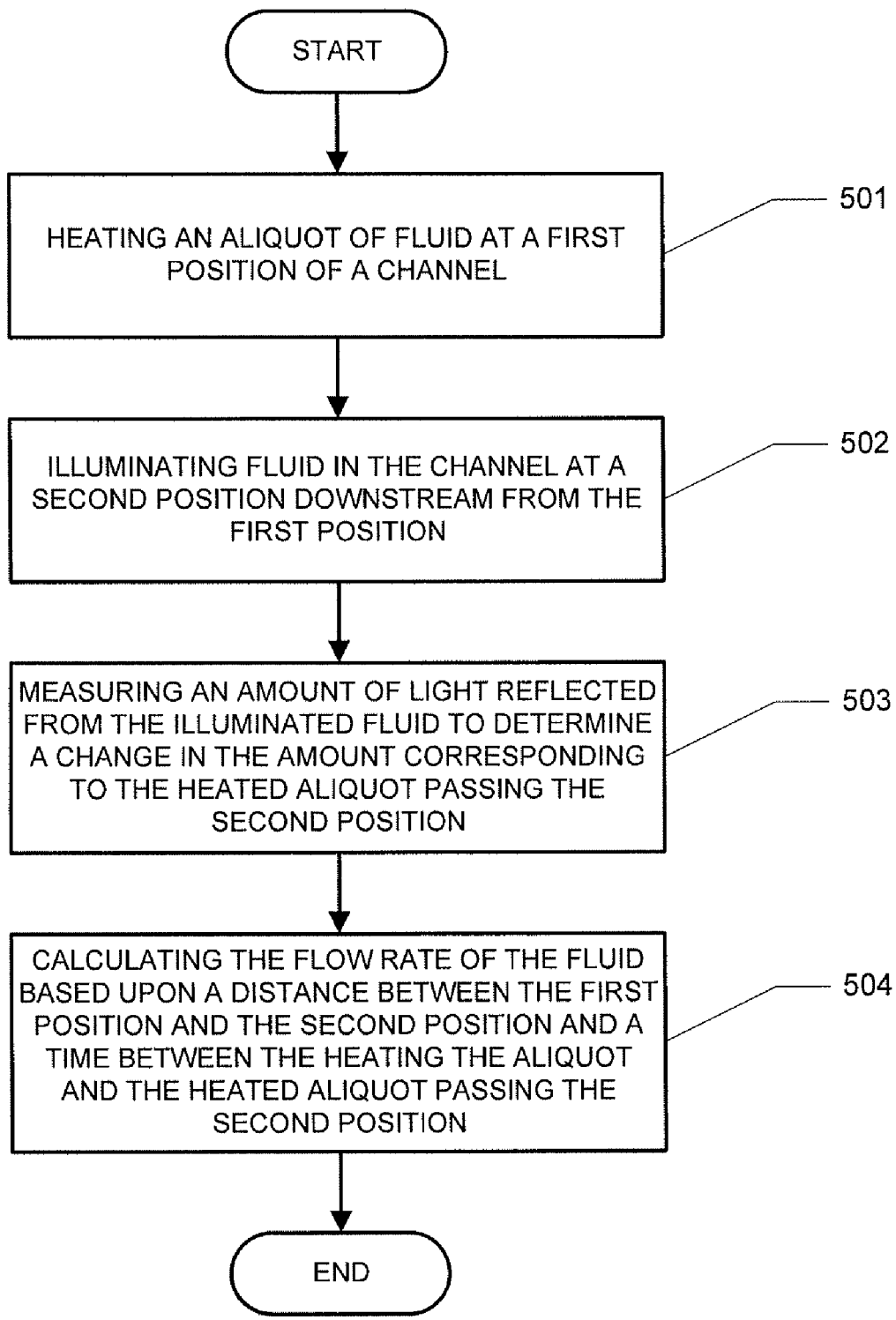
FIG. 5 is a flow chart illustrating a method for determining a flow rate of a fluid according to certain embodiments.

FIG. 5 is a flow chart illustrating a method for determining a flow rate of a fluid in accordance with one embodiment of the present invention. The method begins in step 501, in which an aliquot of fluid is heated at a first position of a fluid-delivery channel. In step 502, fluid in the fluid-delivery channel is illuminated at a second position, downstream from the first position. The amount of light reflected from the illuminated fluid is measured in step 503 to determine a change in the amount corresponding to the heated aliquot passing the second position. In step 504, the flow rate of the fluid is calculated based upon a distance between the first position and the second position, and upon a time between heating the aliquot and the heated aliquot passing the second position.

Figure 6:
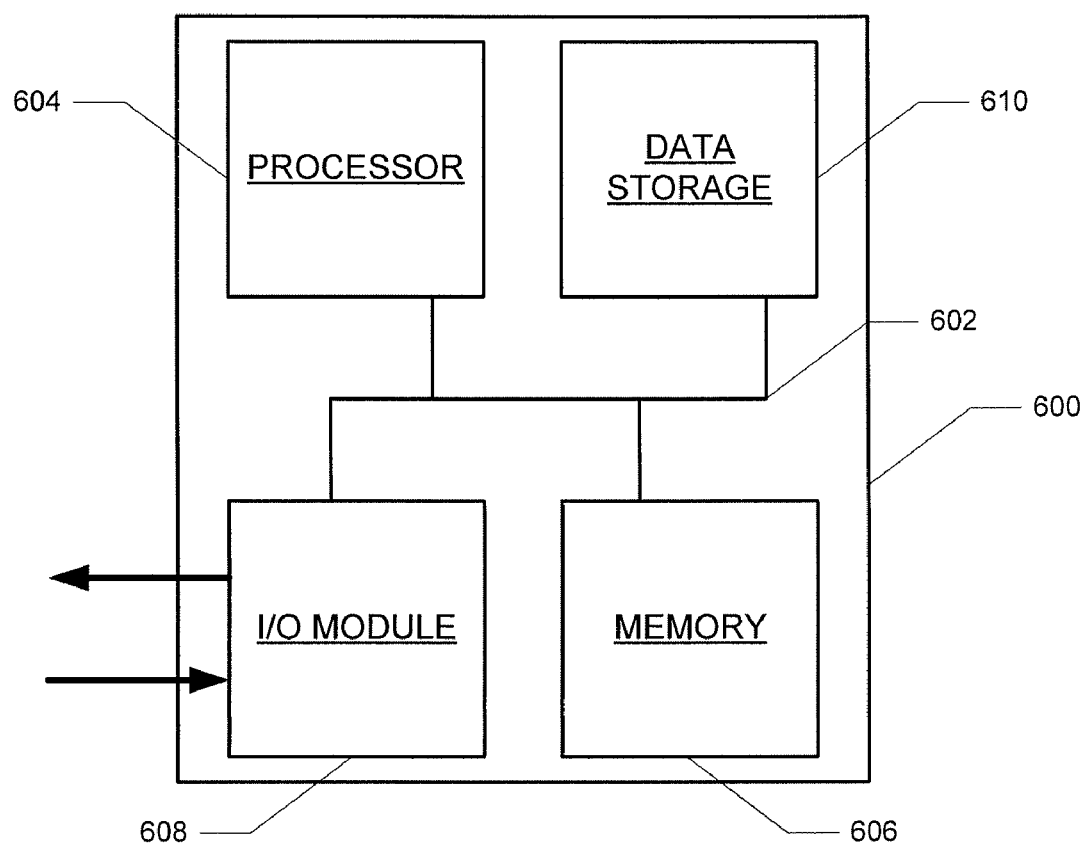
FIG. 6 is a block diagram illustrating a computer system upon which certain embodiments may be implemented.

FIG. 6 is a block diagram that illustrates a computer system 600 upon which certain embodiments may be implemented. Computer system 600 includes a bus 602 or other communication mechanism for communicating information, and a processor 604 coupled with bus 602 for processing information. Computer system 600 also includes a memory 606, such as a random access memory ("RAM") or other dynamic storage device, coupled to bus 602 for storing information and instructions to be executed by processor 604. Memory 606 may also be used for storing temporary variables or other intermediate information during execution of instructions by processor 604. Computer system 600 further includes a data storage device 610, such as a magnetic disk or optical disk, coupled to bus 602 for storing information and instructions.

Computer system 600 may be coupled via I/O module 608 to a display device (not illustrated), such as a cathode ray tube ("CRT") or liquid crystal display ("LCD") for displaying information to a computer user. An input device, such as, for example, a keyboard or a mouse may also be coupled to computer system 600 via I/O module 608 for communicating information and command selections to processor 604.

According to certain embodiments, determining a flow rate of a fluid is performed by a computer system 600 in response to processor 604 executing one or more sequences of one or more instructions contained in memory 606. Such instructions may be read into memory 606 from another machine-readable medium, such as data storage device 610. Execution of the sequences of instructions contained in main memory 606 causes processor 604 to perform the process steps described herein. One or more processors in a multi-processing arrangement may also be employed to execute the sequences of instructions contained in memory 606. In alternative embodiments, hard-wired circuitry may be used in place of or in combination with software instructions to implement various embodiments. Thus, embodiments are not limited to any specific combination of hardware circuitry and software.

The term "machine-readable medium" as used herein refers to any medium that participates in providing instructions to processor 604 for execution. Such a medium may take many forms, including, but not limited to, non-volatile media, volatile media, and transmission media. Non-volatile media include, for example, optical or magnetic disks, such as data storage device 610. Volatile media include dynamic memory, such as memory 606. Transmission media include coaxial cables, copper wire, and fiber optics, including the wires that comprise bus 602. Transmission media can also take the form of acoustic or light waves, such as those generated during radio frequency and infrared data communications. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

The foregoing description is provided to enable any person skilled in the art to practice the various embodiments described herein. While the foregoing embodiments have been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. An optical flow sensor, comprising:
   a heater configured to heat an aliquot of fluid in an adjacent fluid-delivery channel; and
   a sensor disposed adjacent to the fluid-delivery channel downstream from the heater, the sensor configured to illuminate fluid in the fluid-delivery channel, to collect reflected light from the illuminated fluid, and to determine when the heated aliquot passes the sensor based upon a change in an amount of the reflected light,
   wherein the sensor comprises a light source positioned to emit light towards the fluid-delivery channel, and
   wherein the light emitted from the light source does not refract before contact with the fluid-delivery channel.

2. The optical flow sensor according to claim 1, further comprising a processor configured to calculate a flow rate of the fluid in the fluid-delivery channel based upon a time between the heater heating the aliquot and the sensor determining when the heated aliquot passes the sensor.

3. The optical flow sensor according to claim 1, wherein the light source comprises a light emitting diode (LED) optically coupled to the fluid-delivery channel by a first fiber and a photodetector optically coupled to the fluid-delivery channel by a second fiber.

4. The optical flow sensor according to claim 3, wherein the first fiber and the second fiber are disposed on a same side of the fluid-delivery channel.

5. The optical flow sensor according to claim 3, wherein the LED and the photodetector are disposed on a same side of the fluid-delivery channel.

6. The optical flow sensor according to claim 1, wherein the heater is a laser.

7. The optical flow sensor according to claim 1, wherein the fluid is opaque.

* * * * *